US008613957B2

(12) United States Patent
Sigurjonsson et al.

(10) Patent No.: US 8,613,957 B2
(45) Date of Patent: Dec. 24, 2013

(54) SCAFFOLD MATERIAL FOR WOUND CARE AND/OR OTHER TISSUE HEALING APPLICATIONS

(75) Inventors: Gudmundur Fertram Sigurjonsson, Reykjavik (IS); Dora Hlin Gisladottir, Isafjordur (IS); Gudmundur Gudmundsson, Reykjavik (IS)

(73) Assignee: Kerecis EHF, Reykjavik (IS)

(*) Notice: Subject to any disclaimer, the term of this patent is extended or adjusted under 35 U.S.C. 154(b) by 318 days.

(21) Appl. No.: 12/899,123

(22) Filed: Oct. 6, 2010

(65) Prior Publication Data

US 2011/0244054 A1 Oct. 6, 2011

Related U.S. Application Data

(60) Provisional application No. 61/249,341, filed on Oct. 7, 2009, provisional application No. 61/353,320, filed on Jun. 10, 2010.

(51) Int. Cl.
*A61K 35/12* (2006.01)
*A61P 17/02* (2006.01)
*C12N 5/00* (2006.01)

(52) U.S. Cl.
USPC ............ 424/572; 424/520; 424/523; 424/574; 435/1.1; 514/801

(58) Field of Classification Search
None
See application file for complete search history.

(56) References Cited

U.S. PATENT DOCUMENTS

| | | | |
|---|---|---|---|
| 4,164,559 A * | 8/1979 | Miyata et al. ................. | 424/428 |
| 4,801,299 A | 1/1989 | Brendel et al. | |
| 5,331,092 A | 7/1994 | Huc et al. | |
| 5,336,616 A | 8/1994 | Livesey et al. | |
| 5,420,248 A * | 5/1995 | Devictor et al. .............. | 530/356 |
| 5,698,228 A | 12/1997 | Takai et al. | |
| 6,206,931 B1 | 3/2001 | Cook et al. | |
| 6,281,007 B1 | 8/2001 | Fofonoff et al. | |
| 6,398,819 B1 | 6/2002 | Bell | |
| 6,541,023 B1 * | 4/2003 | Andre et al. ................. | 424/422 |
| 6,696,074 B2 | 2/2004 | Dai et al. | |
| 6,753,181 B2 | 6/2004 | Atala | |
| 7,354,702 B2 | 4/2008 | Dai et al. | |
| 7,408,095 B2 | 8/2008 | Serbedzija et al. | |
| 7,423,013 B2 | 9/2008 | Lyngstadaas et al. | |
| 7,531,503 B2 | 5/2009 | Atala et al. | |
| 2003/0059460 A1 | 3/2003 | Tabata et al. | |
| 2005/0124034 A1 | 6/2005 | Kawahara et al. | |
| 2005/0186286 A1 | 8/2005 | Takami | |
| 2005/0260612 A1 | 11/2005 | Padmini et al. | |
| 2007/0134305 A1 | 6/2007 | Zilberman | |
| 2009/0036656 A1 | 2/2009 | Lai et al. | |
| 2010/0028396 A1 | 2/2010 | Ward et al. | |
| 2010/0119579 A1 | 5/2010 | Badylak | |
| 2010/0137203 A1 | 6/2010 | Min et al. | |

FOREIGN PATENT DOCUMENTS

CN  1068703  2/1993
EP  0753313 A1  1/1997

OTHER PUBLICATIONS

Escobar, SO; et al; "Topical fish oil in psoriasis—a controlled and blind study" Clinical and Experimental Dermatology, 17, 159-162, 1992.*
Hwang, Jae-Ho; et al; "Purification and characterization of molecular species of collagen in the skin of skate (Raja kenojei)" Food Chemistry, 100, 921-925, 2007.*
Ylönen, Anne; et al ; "Atlantic salmon (*Salmo salar* L.) skin contains a novel kininogen and another cysteine proteinase inhibitor" European Journal of Biochemistry, 266, 1066-1072, 1999.*
Khan, EA; et al; "Evaluation of EDTA and fish skin extract in primary culture of fish liver cells" Methods in Cell Science, 19, 153-159, 1997.*
Hao-Ying Kuo, et al., "Hybrid Living Skin Equivalent of Human Cells and Processed Animal Matrice", Tissue Engineering, Apr. 2001, p. 235.
International Search Report and Written Opinion issued by the European Patent Office on Apr. 13, 2011, in corresponding International application No. PCT/IB2010/002528.
Bottino, M. C. et al., "Freeze-dried acellular dermal matrix graft: Effects of rehydration on physical, chemical, and mechanical properties," Dental Materials 25 (2009) 1109-1115.
Dahms, S.E. et al., "Composition and biomechanical properties of the bladder acellular matric graft: comparative analysis in rate, pig and human," British Journal of Urology, 82 (1998) 411-419.
Ikoma, T. et al., "Physical propoerties of type I collagen extracted from fish scales of *Pagrus major* and *Oreochromis niloticas*," Intl Journal of Bio Macro., 32 (2003) 199-204.
Song, E. et al., "Collagen scaffolds derived from a marine source and their biocompatibility," Biomaterials 27 (2006) 2951-2961.
Yeh, M. I. et al., "A novel native matrix for tissue engineering analysis of cell matrix interaction," XP-000982329.
Badylak S. F., "The Extracellular Matrix as a Biologic Scaffold Material", Biomaterials, 2007, p. 3587-3593, vol. 28, Elsevier Ltd.
Bottino M. C. et al., "Freeze-dried Acellular Dermal Matrix Graft: Effects of Rehydration on Physical, Chemical and Mechanical Properties", Dental Materials, 2009, p. 1109-1115, vol. 25, Elsevier Ltd.
Dahms S. E. et al., "Composition and Biomechanical Properties of the Bladder Acellular Matrix Graft: Comparative Analysis in Rat, Pig and Human", British Journal of Urology, 1998, p. 411-419, vol. 82.
Ikoma T. et al., "Physical Properties of Type I Collagen Extracted from Fish Scales of *Pagrus major* and *Oreochromis niloticas*", International Journal of Biological Macromolecules, 2003, p. 199-204, vol. 32, Elsevier B.V.

(Continued)

*Primary Examiner* — Blaine Lankford
*Assistant Examiner* — David Berke-Schlessel
(74) *Attorney, Agent, or Firm* — Workman Nydegger (57) ABSTRACT

A scaffold material for wound care and/or other tissue healing applications and methods for making the same is described. The scaffold material is constituted of a decellularized extracellular matrix from fish skin. The scaffold material may also include lipids from the lipid layer of the fish skin. Methods for making and using the scaffold material are also described.

13 Claims, 3 Drawing Sheets

(56) References Cited

OTHER PUBLICATIONS

Singapore Search Report and Wriiten Opinion for Singapore Application No. 201202431-1, mailed May 3, 2013, Danish Patent and Trademark Office, Taastrup, Denmark.
Song E. et al., "Collagen Scaffolds Derived from a Marine Source and their Biocompatibility", Biomaterials, 2006, p. 2951-2961, vol. 27, Elsevier Ltd.
Yeh M. I. et al., "A Novel Native Matrix for Tissue Engineering. Analysis of Cell-Matrix Interaction", FASEB Journal, Federation of American Societies for Experimental Biology, Mar. 15, 2000, p. A444, vol. 14, No. 4.
Tel Aviv University, New Wound Dressing, Full of Antibiotics, Dissolves When Wound Has Healed, Science Daily, sciencedaily.com/releases/2009/11/091117124015.htm.
Dr. Meital Zilberman, Novel Composite Fibers With Drug Delivery for Medical Implants and Tissue Regeneration Applications, The Biomaterials Laboratory, www.eng.tau.ac.il/~meitalz/biomaterials/index2.html, May 10, 2007.
TEI Biosciences, PriMatrix Dermal Repair Scaffold, www.teibio.com, Product Summary.
Promogran, Protease Modulating Matrix, www.systagenix.com/global/our-products/promogran.
Kathleen D. Schaum, MS et al.; A Clinical and Coding Overview of Oasis Wound Matrix and Oasis Burn Matrix, www.healthpoint.com.

\* cited by examiner

SCAFFOLD MATERIAL FOR WOUND CARE AND/OR OTHER TISSUE HEALING APPLICATIONS

RELATED APPLICATIONS

This application claims benefit of U.S. Provisional Application Nos. 61/249,341, filed on Oct. 7, 2009; and 61/353,320, filed on Jun. 10, 2010, the entire contents of which are incorporated herein by reference.

FIELD

This invention relates to a scaffold material for wound care and/or other tissue healing applications and methods for making the same. The scaffold material comprises a decellularized extracellular matrix from fish skin.

BACKGROUND

A variety of human, animal and synthetic materials are currently described or used in medical procedures to augment, repair, or correct tissue defects.

For example, U.S. Published Patent Application No. 2003/0059460 discloses a hybrid polymer material comprising synthetic and natural polymers that can be used in regenerating living body tissue. The hybrid comprises a cross-linked naturally-occurring polymer and a biodegradation-absorbable synthetic polymer. A series of complicated process steps, however, must be undertaken to produce the hybrid material. In addition, the resulting hybrid material contains synthetic as well as naturally-occurring materials.

U.S. Pat. No. 6,541,023 describes the use of porous collagen gels derived from fish skin for use as tissue engineering scaffolds. Preparation of the collagen gels involves grinding the fish skin. Additionally, China Patent No. 1068703 describes a process for preparing fish skin for dressing burn wounds, involving separating fish skin from the fish body and placing the skin in a preservation solution of iodine tincture, ethanol, borneol, sulfadiazine zinc and hydrochloric acid in amounts sufficient to establish a pH value of 2.5-3. However, these products can be difficult to handle as the product of U.S. Pat. No. 6,541,023 is in a gel form and the product of China Patent No. 1068703 is stored in a solution.

In addition, a number of extracellular matrix products for medical uses have been derived from human skin (ALLODERM® Regenerative Tissue Matrix (LifeCell)); fetal bovine dermis (PRIMATRIX™ Dermal Repair Scaffold (TEI Biosciences)); porcine urinary bladder (MATRISTEM™ Extracellular Matrix Wound Sheet (Medline Industries, Inc.)); and porcine small intestinal submucosa (OASIS® Wound Matrix (Healthpoint Ltd.)). However, there is a need for improved products and methods to enhance wound healing and tissue repair. The present invention satisfies this need.

SUMMARY

The extracellular matrix (ECM) of vertebrates is a complex structural entity surrounding and supporting cells. ECM is composed of complex mixtures of structural proteins, the most abundant of which is collagen, and other specialized proteins and proteoglycans. The scaffold material described herein is a largely intact acellular scaffold of natural biological ECM components from fish skin. The scaffold can also comprise naturally-occurring lipids from the fish skin. The native three-dimensional structure, composition, and function of the dermal ECM is essentially unaltered, and provides a scaffold to support cell migration, adherence, proliferation, and differentiation, thus facilitating the repair and/or replacement of tissue. The present invention also relates to methods of making and of using the scaffold material.

BRIEF DESCRIPTION OF THE DRAWINGS

FIG. 2 shows optical images of scaffold material cross-sections at 100× (2A) and 400× (2B) magnification.

FIG. 3 shows scanning electron microscope (SEM) images of scaffold material cross-sections at 300× (3A) and 600× (3B) magnification.

DESCRIPTION

Figure 1:
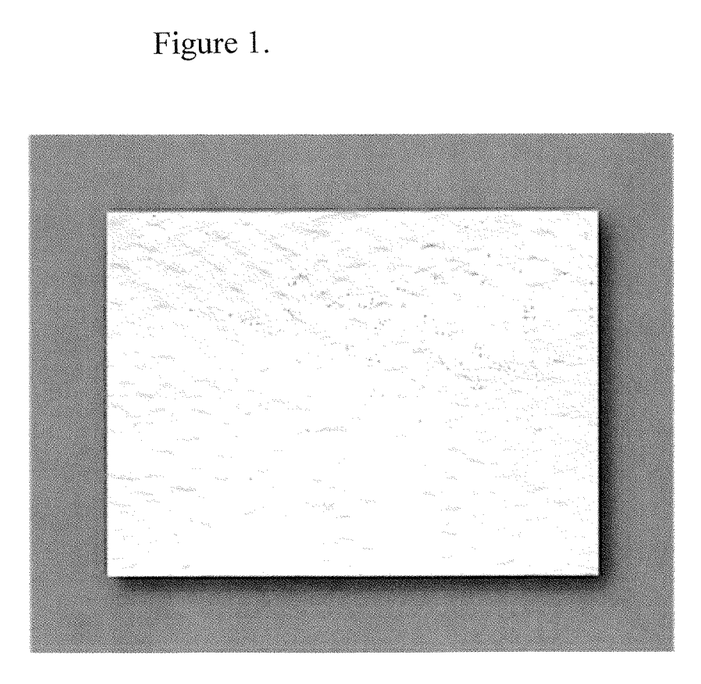
FIG. 1 shows an illustrative sample of a decellularized ECM product (scaffold material) made from fish skin in accordance with a process described herein.
Figure 2:
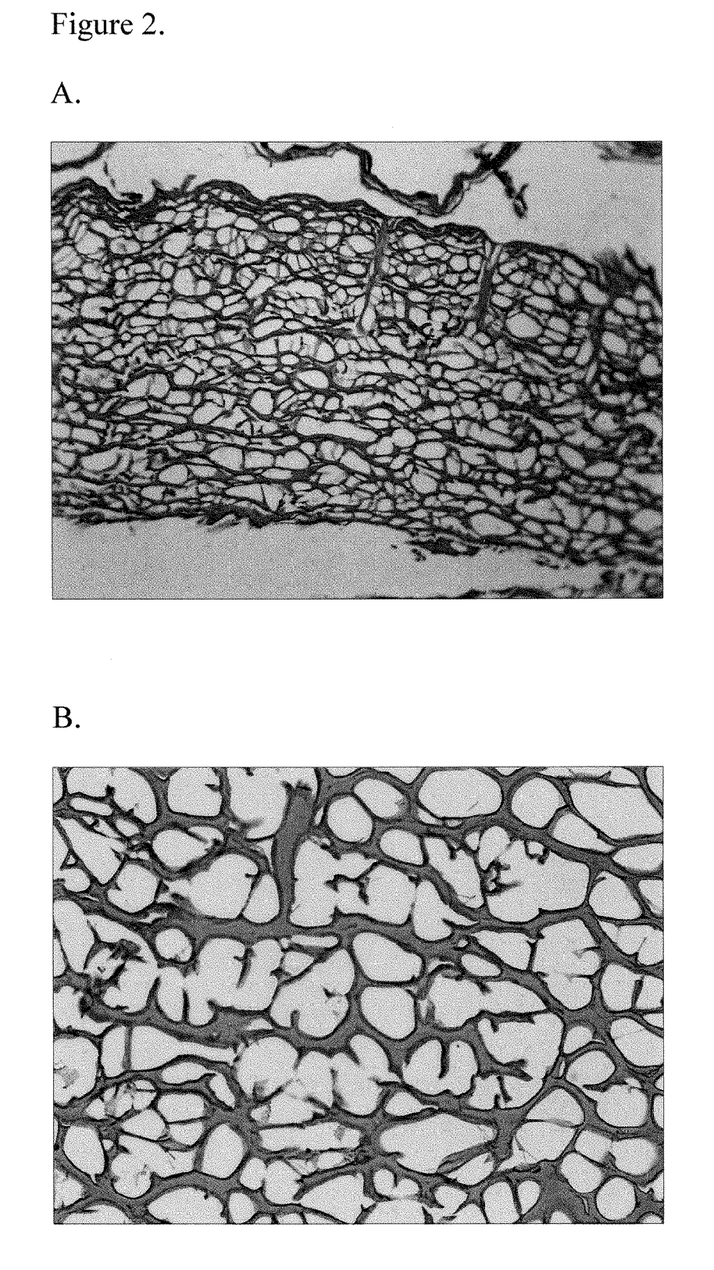
Figure 3:
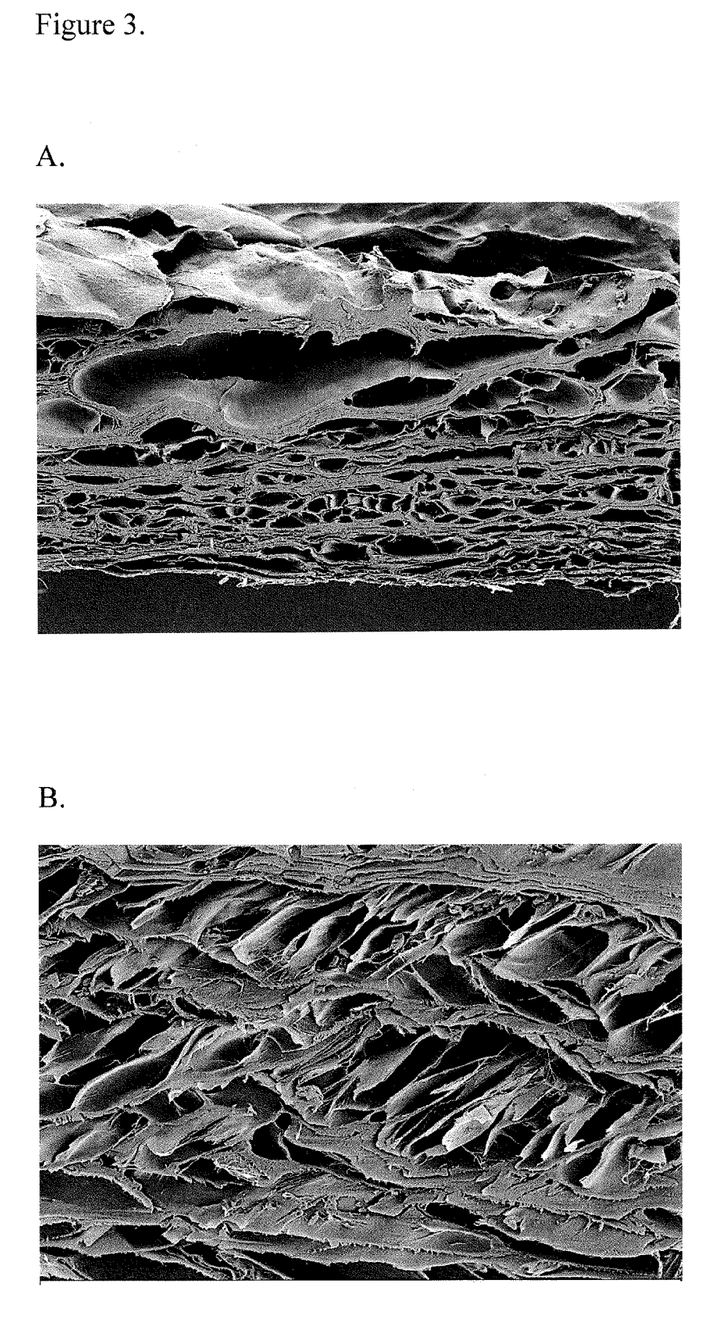

A scaffold material in accordance with this invention is obtained from intact fish skin. An illustrative example showing the appearance of a sample of the scaffold material is shown in FIG. 1. Any species of fish, including bony or cartilaginous fish, can be used as the source of the fish skin. For example, the source can be round fish like cod, haddock and catfish; flatfish, like halibut, plaice and sole; salmonids like salmon and trout; scombridaes like tuna; or small fish like herring, anchovies, mackerel and sardines. In certain embodiments the fish skin is obtained from cold-water oily fish and/or fish known to contain high amounts of omega-3 oil. Examples of fish high in omega-3 oil are salmon, pilchards, tuna, herring, cod, sardines, mackerel, sable fish, smelts, whitefish, hoki fish, and some varieties of trout.

The fish skin is removed from the fish before processing. If the fish skin is from a species of fish that has scales, the fish skin should be de-scaled so that a substantial portion of the scales are removed or at least the hydroxyapatite removed from the scales. The phrase "a substantial portion of the scales are removed" or "substantially scale-free" means that at least 95%, preferably at least 99%, and more preferably 100% of the scales on the fish skin are removed. "Substantially scale free" fish skin can also refer to fish skin from a fish species without scales. The scales are either removed prior to all processing, with purely mechanical pressure (via, e.g., knife, shaking with abrasives, water pressure, a special scale removal device that uses the same mechanical force as knives or other pressure device, like polishing with ceramic or plastic) or after some chemical treatment (e.g. decellularization) and then with mechanical pressure in order to wash the scales away. If the fish skin is first treated chemically and/or enzymatically (e.g. treatment with TRITON® X-100), the mechanical pressure generally needs to be gentle since the skin is more vulnerable to tearing after decellularization. The scales can be removed in more than one step, for example partial removal prior to decellularization followed by further removal during and/or after decellularization. Alternatively the scales can be removed by chemical treatment alone.

After the scales have been removed, the fish skin is optionally frozen prior to decellularization. The fish skin can be frozen quickly by incubating the skin in liquid nitrogen or using other special freezing equipment that can freeze the skin to −70° C. or lower, in order to preserve the collagen structure of the scaffold. Alternatively, the fish skin can be frozen in a conventional type of freezer that would be typically found in a fish factory. The freezing process may lyse or partially lyse the cells comprising the intact fish skin, and help facilitate decellularization of the fish skin. If the fish skin has been frozen, it can later be thawed for further processing.

Whether or not the fish skin was frozen, it can be washed with a buffer solution prior to further processing. For example, the fish skin can be washed 1-3 times with a buffer solution optionally containing one or more antioxidants (e.g. ascorbic acid (such as 50 mM ascorbic acid), Vitamins A, C, E, and beta carotene), antibiotics (e.g., streptomycin and penicillin), proteases (e.g. dispase II) and protease inhibitors (e.g. antipain, aprotinin, benzamidine, bestatin, DFP, EDTA, EGTA, leupeptin, pepstatin, phosphoramidon, and PMSF) to facilitate disinfection and stabilization of the fish skin. The buffer solution can be at a pH of at least 5.5, such as 6.0, 6.5, 7.0, 7.5, 8.0, 8.5, 9.0, 9.5, 10.0 or more. In certain embodiments the pH is between 7.0 and 9.0, e.g. between 7.5 and 8.5. The buffer solution can also be used as a medium in which the fish skin can be stored for a few days up to a few weeks or more. In certain embodiments the fish skin is stored in the buffer solution at a temperature of about 4° C.

After freezing and/or washing and/or storage in a buffer solution, the fish skin is treated with one or more decellularizing solutions to remove cellular material, including antigenic material, from the fish skin with minimal to no damage to the mechanical and structural integrity and biological activity of the naturally occurring extracellular matrix.

The terms "extracellular matrix" or "ECM" as used herein refer to the non-cellular tissue material present within the fish skin that provides structural support to the skin cells in addition to performing various other important functions. The ECM described herein does not include matrix material that has been constituted or re-formed entirely from extracted, purified, or separated ECM components (e.g. collagen).

The terms "acellular," "decellularized," "decellularized fish skin," and the like as used herein refer to a fish skin from which a substantial amount of cellular and nucleic acid content has been removed leaving a complex three-dimensional interstitial structure of ECM. "Decellularizing agents" are those agents that are effective in removing a substantial amount of cellular and nucleic acid content from the ECM. The ECM is "decellularized" or "substantially free" of cellular and nucleic acid content (i.e. a "substantial amount" has been removed) when at least 50% of the viable and non-viable nucleic acids and other cellular material have been removed from the ECM. In certain embodiments, about 55%, 60%, 65%, 70%, 75%, 80%, 85%, 90%, 91%, 92%, 93%, 94%, 95%, 96%, 97%, 98%, 99%, 99.5%, or 100% of the viable and non-viable nucleic acids and cellular material are removed. Decellularization can be verified by, for example, testing the treated fish skin for DNA content. Removal of the nucleic acids from the ECM can be determined, for example, by histological examination of the ECM, and/or by a biochemical assay such as the PICOGREEN® assay, diphenylamine assay, or by PCR.

Decellularization disrupts the cell membranes and releases cellular content. Decellularizing may involve one or more physical treatments, one or more chemical treatments, one or more enzymatic treatments, or any combination thereof. Examples of physical treatments are sonication, mechanical agitation, mechanical massage, mechanical pressure, and freeze/thawing. Examples of chemical decellularizing agents are ionic salts (e.g. sodium azide), bases, acids, detergents (e.g. non-ionic and ionic detergents), oxidizing agents (e.g. hydrogen peroxide and peroxy acids), hypotonic solutions, hypertonic solutions, chelating agents (e.g. EDTA and EGTA), organic solvents (e.g. tri(n-butyl)-phosphate), ascorbic acid, methionine, cysteine, maleic acid, and polymers that bind to DNA (e.g. Poly-L-lysine, polyethylimine (PEI), and polyamindoamine (PAMAM)). Non-ionic detergents include 4-(1,1,3,3-Tetramethylbutyl)phenyl-polyethylene glycol, t-Octylphenoxypolyethoxyethanol, Polyethylene glycol tert-octylphenyl ether (TRITON® X-100) (Dow Chemical Co.). Ionic detergents include sodium dodecyl sulfate (SDS), sodium deoxycholate, TRITON® X-200, and zwitterionic detergents (e.g. CHAPS). Other suitable decullularizing detergents include polyoxyethylene (20) sorbitan mono-oleate and polyoxyethylene (80) sorbitan mono-oleate (Tween 20 and 80), 3-[(3-chloramidopropyl)-dimethylammino]-1-propane-sulfonate, octyl-glucoside and sodium dodecyl sulfate. Examples of enzymatic decellularizing agents are proteases, endonucleases, and exonucleases. Proteases include serine proteases (e.g. trypsin), threonine proteases, cysteine proteases, aspartate proteases, metalloproteases (e.g. thermolysin), and glutamic acid proteases. Decellularization is generally carried out at a pH of at least 5.5, such as 6.0, 6.5, 7.0, 7.5, 8.0, 8.5, 9.0, 9.5, 10.0 or more. In certain embodiments the pH is between 7.0 and 9.0, e.g. between 7.5 and 8.5.

An example of a decellularization step is incubating the fish skin in a solution comprising 1 M NaCl, 2% deoxycholic acid, 0.02% sodium azide and 500 ppm streptomycin. In another example, the fish skin is incubated with a first decellularizing solution comprising a protease (e.g., 2.5 U/mL dispase II) and other components (e.g., 0.02% sodium azide). The first decellularizing solution is poured off and the fish skin is then treated with a second decellularizing solution such as a solution comprising a detergent (e.g., 0.5% TRITON® X-100) and other components (e.g. 0.02% sodium azide). In another example, the fish skin is first treated with a decellularizing solution comprising detergent (e.g. 0.5% TRITON® X-100) with other components (e.g. 0.02% EDTA, sodium azide, and/or deoxiholic acid), and then incubated in a second decellularizing solution comprising a detergent such as SDS.

The fish skin may or may not be incubated under shaking The decellularizing step(s) can be repeated as needed by pouring off any remaining decellularizing solution, optionally washing the fish skin with a buffer solution (e.g. Hank's Balanced Salt Solution), and then treating the fish skin again with another step of decellularization. Once a sufficient amount of cell material has been removed, the decellularizing solution can be removed (e.g., by aspiration or by gently pouring out the solution).

After decellularization, the fish skin can optionally be washed with water, buffer solution, and/or salt solution. Examples of suitable washing solutions include Dulbecco's phosphate buffered saline (DPBS), Hank's balanced salt solution (HBSS), Medium 199 (M199, SAFC Biosciences, Inc.) and/or L-glutamine. Washing step(s) are generally carried out at a pH of at least 5.5, such as 6.0, 6.5, 7.0, 7.5, 8.0, 8.5, 9.0, 9.5, 10.0 or more. In certain embodiments the pH is between 7.0 and 9.0, e.g. between 7.5 and 8.5.

The fish skin can optionally be bleached to improve the appearance of the final product. Bleaching can be carried out before, after, and/or concurrently with decellularization. For example, one or more bleaching agent can be incorporated into one or more of the decellularization solution(s) and/or into one or more buffer solution(s). Examples of bleaching agents include sodium sulfite, hydrogen peroxide, ammonium persulfate, potassium persulfate, and sodium persulfate. In certain embodiments, if a strong bleaching agent like persulfate(s) are used, bleaching and decellularization can be combined in a single step comprising incubating the fish skin in a mixture of one or more bleaching agents, thickeners, and peroxide sources. For example, a dry bleaching mixture can be prepared (see, e.g., the "bleaching mixtures" described in Example 5), followed by the addition of water, hydrogen peroxide, or a combination thereof to the dry mixture to form a bleaching solution that may also be sufficient for decellularization. The bleaching agents (e.g. sodium sulfite, hydrogen peroxide, ammonium persulfate, potassium persulfate, and sodium persulfate) should be about 40-60% w/w of the dry mixture. A combination of EDTA and persulfates may be added to the mixture to accelerate bleaching as well as decellularization. In certain embodiments the concentration of EDTA in the dry mixture is about 0.25-5% w/w. Hydrogen peroxide can be about 15-25% of the mixture; the peroxide source can be sodium percarbonate and potassium percarbonate. Sodium phosphate perhydrate and sodium carbonate or magnesium metasilicate and silicium silicate can also be used as a peroxide source. The dry mixture can also include silica and hydrated silica, at for example 1-10% w/w, and optionally one or more stearate (e.g. ammonium stearate, sodium stearate, and/or magnesium stearate). In addition the dry mixture can optionally include thickeners, such as hydroxypropyl methylcellulose, hydroxyethylcellulose, algin (i.e. alginate), organic gums (e.g. cellulose, xanthan gum) sodium metasilicat, and combinations thereof to increase the viscosity of the bleaching/decellularization solution and protect protein fibers from damage. Bleaching, and/or bleaching plus decellularization, is generally carried out at a pH of at least 5.5, such as 6.0, 6.5, 7.0, 7.5, 8.0, 8.5, 9.0, 9.5, 10.0 or more. In certain embodiments the pH is between 7.0 and 9.0, e.g. between 7.5 and 8.5. After bleaching and/or bleaching plus decellularization, the fish skin is optionally washed with a solution comprising L-glutamine under the pH conditions described above.

In certain embodiments, the fish skin is treated with a digestion enzyme. Similar to bleaching, digestion can be carried out before, after, and/or concurrently with decellularization. Suitable enzymes include proteases, for example serine proteases, threonine proteases, cysteine proteases, aspartate proteases, metalloproteases, and glutamic acid proteases. In certain embodiments the digestion enzyme is a serine protease such as trypsin. The digestion enzyme can be an enzyme that functions in an alkaline environment, limits cross-linking within the ECM, and softens the fish skin. Digestion is generally carried out at a pH of at least 5.5, such as 6.0, 6.5, 7.0, 7.5, 8.0, 8.5, 9.0, 9.5, 10.0 or more. In certain embodiments the pH is between 7.0 and 9.0, e.g. between 7.5 and 8.5.

The decellularized fish skin can optionally be cryopreserved. Cryopreservation can involve immersing the fish skin in a cryoprotectant solution prior to freezing. The cryoprotectant solution generally comprises an appropriate buffer, one or more cryoprotectants, and optionally a solvent, e.g. an organic solvent which in combination with water undergoes minimal expansion and contraction. Examples of cryoprotectants include sucrose, raffinose, dextran, trehalose, dimethylacetamide, eimethylsulfoxide, ethylene glycol, glycerol, propylene glycol, 2-Methyl-2.4-pantandial, certain antifreeze proteins and peptides, and combinations thereof. Alternatively, if the decellularized fish skin is fast-frozen (flash-frozen) prior to sublimation in order to minimize ice crystals formed during the freezing step, the skins can optionally be frozen in a buffer solution that does not include cryoprotectants. Cryopreservation is generally carried out at a pH of at least 5.5, such as 6.0, 6.5, 7.0, 7.5, 8.0, 8.5, 9.0, 9.5, 10.0 or more. In certain embodiments the pH is between 7.0 and 9.0, e.g. between 7.5 and 8.5.

The decellularized fish skin can be packaged inside a sterile container, such as a glass vial or a pouch. In one embodiment, a TYVEK® pouch is used. For example, the fish skin can be incubated in a cryoprotectant solution, packaged in a TYVEK® pouch and then placed into a freeze dryer and frozen at a rate which is compatible with the cryoprotectant.

The decellularized fish skin can be lyophilized, i.e. frozen at a low temperature and under vacuum conditions so that water is removed sequentially from each ice crystal phase without ice re-crystallization. During lyophilization, water is generally removed first via sublimation and then via desorption if necessary. Another method of removing excess water after processing and before sterilization is vacuum pressing.

In certain embodiments, the decellularized fish skin is sterilized before and/or after being frozen. Sterilization methods are well known in the art. For example, the decellularized fish skin can be placed in an ethylene oxide chamber and treated with suitable cycles of ethylene oxide. Other sterilization methods include sterilizing with ozone, carbon dioxide, gaseous formaldehyde or radiation (e.g. gamma radiation, X-rays, electron beam processing, and subatomic particles).

As an alternative to or in addition to freezing, freeze-drying and/or vacuum pressing of water, the decellularized fish skin can be preserved in a non-aqueous solution such as alcohol.

The resulting product (scaffold material) is a sterile, collagen-based matrix that possesses properties that may facilitate the regeneration, repair and/or replacement of tissue (e.g., repair, regeneration, and/or growth of endogenous tissue). The term "scaffold material" refers to material comprising fish skin that has been decellularized and optionally bleached, digested, lyophilized, etc. as discussed above. The scaffold material can provide an intact scaffold for support of endothelial and/or epithelial cells, can be integrated by the host, is biocompatible, does not significantly calcify, and can be stored and transported at ambient temperatures. The phrase "integrated by the host" means herein that the cells and tissues of the patient being treated with the scaffold material can grow into the scaffold material and that the scaffold material is actually integrated/absorbed into the body of the patient. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Persistently high levels of matrix metalloproteses (MMPs) may contribute to wound chronicity. The scaffold material described herein may absorb matrix metalloproteses (MMPs) thus promoting wound healing and transition from a chronic to an acute wound.

The scaffold material contains proteins from the extracellular matrix (ECM) of the fish skin. The ECM components in the scaffold material can include, for example, structural proteins; adhesive glycoproteins; proteoglycans; non-proteoglycan polysaccharides; and matricellular proteins. Examples of structural proteins include collagens (the most abundant protein in the ECM), such as fibrillar collagens (types I, II, III, V, and XI); facit collagens (types IX, XII, and XIV), short chain collagens (types VIII and X), basement membrane collagen (type IV), and other collagens (types VI, VII, and XIII); elastin; and laminin. Examples of adhesive glycoproteins include fibronectin; tenascins; and thrombospondin. Examples of proteoglycans include heparin sulfate; chondroitin sulfate; and keratan sulfate. An example of a non-proteoglycan polysaccharide is hyaluronic acid. Matricellular proteins are a structurally diverse group of extracellular proteins that regulate cell function via interactions with cell-surface receptors, cytokines, growth factors, proteases, and the ECM. Examples include thrombospondins (TSPs) 1 and 2; tenascins; and SPARC (secreted protein, acidic and rich in cysteine).

In certain embodiments, decellularization (and other optional processing steps) does not remove all of the naturally-occurring lipids from the lipid layer of the fish skin. Thus, the scaffold material can comprise one or more lipids from the fish skin, particularly from the lipid layer of the fish skin. For example, the scaffold material may include up to about 25% w/w lipids (of dry weight of the total scaffold material after lyophilization), such as 0.1%, 0.5%, 1%, 2%, 3%, 4%, 5%, 6% 7%, 8%, 9%, 10%, 11%, 12%, 13%, 14%, 15%, 16%, 17%, 18%, 19%, 20%, 21%, 22%, 23%, or 24% w/w lipids. The presence of lipids in the scaffold material can be verified, for example, by organic solvent extraction followed by chromatography. Examples of suitable organic solvents include acetone and chlorphorm.

The lipids in the scaffold material can include, for example, fatty acyls (i.e. fatty acids, their conjugates, and deriviates); glycerolipids; glycerophospholipids (i.e. phospholipids); sphingolipids; saccharolipids; polyketides; sterol lipids (i.e. sterols); certain fat-soluble vitamins; prenol lipids; and/or polyketides. Examples of fatty acyls include saturated fatty acids, such as polyunsaturated fatty acids; fatty esters; fatty amides; and eicosanoids. In certain embodiments the fatty acids include omega-3 fatty acids, such as eicosapentaenoic acid (EPA) and docosahexaenoic acid (DHA) (found in high concentration in fish oil). Other fatty acids found in fish oil include arachidic acid, gadoleic acid, arachidonic acid, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, and lignoceric acid. Examples of glycerolipids include mono-, di-, and tri-substituted glycerols, such as monoacylglycerols, diacylglycerols, and triacylglycerols (i.e. monoglycerides, diglycerides, and triglycerides). Examples of glycerophospholipids include phosphatidylcholine; phosphatidylethanolamine; and phosphatidylserine. Examples of sphingolipids include phosphosphingolipids and glycosphingolipids. Examples of sterol lipids include cholesterol; steroids; and secosteroids (various forms of Vitamin D). Examples of prenol lipids include isoprenoids; carotenoids; and quinones and hydroquinones, such as Vitamins E and K.

The scaffold material can contain one or more added active agents (i.e an agent that is added during or after processing of the scaffold material), such as antibiotics, antiseptics, antimicrobial agents, antivirals, antifungals, antiparasitics and anti-inflammatory agents. The active ingredient can be a compound or composition that facilitates wound care and/or tissue healing such as an antioxidant, or drug. It can also be a protein or proteins and/or other biologics. Antibiotics, antiseptics, and antimicrobial agents can be added in an amount sufficient to provide effective antimicrobial properties to the scaffold material. In certain embodiments, the antimicrobial agent is one or more antimicrobial metal, such as silver, gold, platinum, copper, zinc, or combinations thereof. For example, silver may be added to the scaffold material during processing in ionic, metal, elemental, and/or colloidal form. The silver may also be in combination with other antimicrobials. Anti-inflammatory agents can be added in an amount sufficient to reduce and/or inhibit inflammation at the wound or tissue area where the scaffold material is applied.

The scaffold material can be used in dried form. Alternatively, the scaffold material can be rehydrated prior to use. In certain embodiments, one or more scaffold materials are laminated together to form a thicker scaffold material.

Generally, the scaffold material is from about 0.1 to 4.0 mm thick (i.e. in cross-section), such as 0.5, 1.0, 1.5, 2.0, 2.5, 3.0 or 3.5 mm thick. The thickness can depend on a number of factors, including the species of fish used as the starting material, processing, lyophilization, and/or rehydration (see Example 14). Of course, the thickness is proportionately greater when the product comprises more than one layer of scaffold material.

The scaffold material described herein can be used for a variety of medical applications. For example, the scaffold material can be used as a wound dressing and/or as a suture material, wherein the scaffold material is applied on or to a portion of a wound or tissue area. The term "wound" refers to any injury resulting in tissue damage, tissue penetration, laceration, or lesions. The wounds amenable to treatment by the scaffold material include injuries that can be located in any site, including internal, interfacial, external, interstitial, extracorporeal, and/or intracorporeal. Examples of wounds suitable for coverage with the scaffold material include cuts, gashes, open wounds, tissue rupture, Decubitus, Dermatitis, lesions, chronic wounds, battlefield wounds, necrotic wounds, acute, chronic, traumatic, lacerations, abrasions, contusions, necrotizing facitis, toxic epidermal nercolysis, pressure wounds, venous insufficiency ulcers, arterial ulcers, diabetic or neuropathic ulcers, pressure ulcers, mixed ulcers, burn wounds, Mucormycosis, Vasculitic wounds, Pyoderma, gangrenosum, and equivalents, and/or combinations thereof, known by persons skilled in the art. Treatment of wounds in human and animal subjects are contemplated.

In certain embodiments, the scaffold material is used for abdominal wall reconstruction, for example to repair hernias. For example, in repairing a hernia, a surgeon will make an incision near the location of the hernia. For an inguinal hernia, the incision is made just above the crease where the abdomen meets the thigh. To repair an umbilical hernia, it is made close to the navel. If the hernia has occurred at the site of a previous operation, the incision from that surgery is reopened. Surgery proceeds in much the same way, regardless of where the incision is made. The hernia sac is carefully opened and the intestine or other tissue is placed back inside the abdomen. The weakened area is repaired and reinforced with a synthetic mesh or a suture that pulls the abdominal muscle tissue back together.

The scaffold material described herein can be used as a mesh material or suture, or used to strengthen a mesh material or suture. The scaffold material can be used to reinforce or enhance a wound care or tissue healing product such as a wound dressing, a mesh material, a bandage, or a suture. For example, the scaffold material can be used next to or be intertwined with a wound dressing, a mesh material or a suture. When used as a mesh material or suture, or to strengthen a mesh material or suture, the scaffold material may be treated to increase cross-linking of the component ECM materials, using, e.g., chemical cross-linkers such as gluteraldehyde or chromium. The scaffold material can also be used to replace lost gingiva due to periodontal disease, form a bladder sling, and facilitate pelvic floor reconstruction.

As used herein, the singular forms "a", "an" and "the" include plural referents unless the context clearly dictates otherwise.

The publications disclosed herein are provided solely for their disclosure prior to the filing date of the present application. Nothing herein should be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference in their entirety.

While the disclosure has been described in detail with reference to certain embodiments thereof, it will be apparent to one skilled in the art that various changes can be made, and equivalents employed, without departing from the scope of the disclosure. In addition, the following examples are illustrative only and should not be considered as limiting the disclosure in any way.

EXAMPLES

Example 1

Skin Removal

The skin was removed from a fish fillet, along with as much epidermal fat as possible.

The fish skin was descaled on a cutting board by scraping the surface of the fish skin with a knife.

Disinfection and Stabilization

The descaled skin was washed two times for 1 h at 4° C. with sterile phosphate-buffered saline containing 50 mM ascorbic acid, 500 ppm streptomycin, respectively.

Decellularization a) The fish skin was placed in 1 M NaCl for 8 h followed by incubation in 2% deoxycholic acid containing 0.02% sodium azide and 500 ppm streptomycin.

b) The solution in a) was poured off. The fish skin was placed in Hank's Balanced Salt Solution for 10 min at 40 RPM at room temperature. The step was repeated and the fish skin was placed in a container in a laminar flow hood, opened and the solution was aspirated off. The procedure was repeated two more times.

c) The fish skin was treated with a decellularizing solution containing 0.5% SDS, and the container was placed on a rotator at 40 RPM for 1 h at room temperature.

d) The decellularizing solution was removed as described in b) by aspiration. The fish skin was washed with 50 mL of Dulbecco's phosphate buffered saline.

Digestion

The fish skin was incubated for 18 h at room temperature in a digestion solution which consisted of 1 M Tris-HCl, trypsin at 0.05 µg/mL, at a pH of 8.5.

Cryoprotection

The fish skin was immersed in a pre-freezing solution containing 7% dextran, 6% sucrose, 6% raffinose and 1 mM EDTA in Hank's Balanced Salt Solution.

Washing

The fish skin was washed with the pre-freezing solution and placed in a rotator at 40 RMP for 120 min at room temperature.

Packaging

The fish skin was inserted into a pouch that was heat sealed shut. The pouch was a medical grade porous TYVEK® membrane pouch from DuPont, suitable for sterilization with Ethylene Oxide (EtOx).

Lyophilization

The pouch containing the fish skin was inserted into a freeze dryer and freeze dried.

Sterilization

The pouch containing the fish skin was inserted into an ethylene oxide chamber and treated with 1 to 5 cycles of ethylene oxide to sterilize the fish skin.

Example 2

Skin Removal

The skin was removed from a fish fillet, along with as much epidermal fat as possible.

The fish skin was descaled on a cutting board by scraping the surface of the fish skin with a knife.

Disinfection and Stabilization

The descaled skin was washed two times for 1 h at 4° C. with sterile phosphate-buffered saline containing 50 mM ascorbic acid, 500 ppm streptomycin, respectively.

Decellularization a) The fish skin was placed in phosphate buffered saline containing 2.5 U/mL dispase II (or pronase) and 0.02% sodium azide and incubated at 4° C. for 8 h with continuous shaking. The solution was then poured off and the sample was incubated under gentle shaking in a second solution of 0.5% TRITON® X-100 and 0.02% sodium azide for 24 h.

b) The second solution in a) was poured off. The fish skin was placed in Hank's Balanced Salt Solution for 10 min at 40 RPM at room temperature. The step was repeated and the fish skin was placed in a container in a laminar flow hood, opened and the solution was aspirated off. The procedure was repeated two more times.

c) The fish skin was treated with a decellularizing solution containing 0.5% SDS, and the container was placed on a rotator at 40 RPM for 1 h at room temperature.

d) The decellularizing solution of c) was removed as described in b) by aspiration. The fish skin was washed with 50 mL of Dulbecco's phosphate buffered saline.

Digestion

The fish skin was incubated for 18 h at room temperature in a digestion solution of 1 M Tris-HCl, trypsin at 0.05 µg/mL, at a pH of 8.5.

Cryoprotection

The fish skin was immersed in a pre-freezing solution containing 7% dextran, 6% sucrose, 6% raffinose and 1 mM EDTA in Hank's Balanced Salt Solution.

Washing

The fish skin was washed with the pre-freezing solution and placed in a rotator at 40 RMP for 120 min at room temperature.

Packaging

The fish skin was inserted into a TYVEK® membrane pouch and heat sealed shut.

Lyophilization

The pouch containing the fish skin was inserted into a freeze dryer and freeze dried.

Sterilization

The pouch containing the fish skin was inserted into an ethylene oxide chamber and treated with 1 to 5 cycles of ethylene oxide to sterilize the fish skin.

Example 3

Skin Removal

The skin was removed from a fish fillet, along with as much epidermal fat as possible.

The fish skin was descaled on a cutting board by scraping the surface of the fish skin with a knife.

Freezing

The fish skins were frozen in a standard fish-factory fast-freezer. During the freezing process the cells lysed. Freezing inhibits microbial growth.

Thawing

Fish skins were thawed at 4° C.

Disinfection and Stabilization

The descaled skin was washed two times for 1 h at 4° C. with sterile phosphate-buffered saline containing 50 mM ascorbic acid, 500 ppm streptomycin, respectively.

Decellularization a) The fish skin was treated with a decellularizing solution containing 0.5% SDS, and the container was placed on a rotator at 40 RPM for 1 h at room temperature.

b) The decellularizing solution was removed by aspiration. The fish skin was washed with 50 mL of Dulbecco's phosphate buffered saline.

Digestion

The fish skin was incubated for 18 h at room temperature in a digestion solution of 1 M Tris-HCl, trypsin at 0.05 μg/mL, at a pH of 8.5.

Cryoprotection

The fish skin was immersed in a pre-freezing solution containing 7% dextran, 6% sucrose, 6% raffinose and 1 mM EDTA in Hank's Balanced Salt Solution.

Washing

The fish skin was washed with a pre-freezing solution and placed in a rotator at 40 RMP for 120 min at room temperature.

Packaging

The fish skin was inserted into a TYVEK® membrane pouch and heat sealed shut.

Lyophilization

The pouch containing the fish skin was inserted into a freeze dryer and freeze dried.

Sterilization

The pouch containing the fish skin was inserted into an ethylene oxide chamber and treated with 1 to 5 cycles of ethylene oxide to sterilize the fish skin.

Example 4

Fish skins were processed as described in each of examples 1-3, except that a bleaching agent (sodium sulfite) was also added to the pre-freezing solution at 0.5% concentration in the washing step to obtain a bleached scaffold matrix.

Example 5

Bleaching/decellularization mixtures were prepared as follows:

| Bleaching mixture A | |
| --- | --- |
| Glyceryl stearate | 5% |
| Ammonium persulfate | 20% |
| EDTA | 0.5% |
| Xanthan gum | 3.5% |
| Potassium persulfate | 46% |
| Silica | 2% |
| Hydrated silica | 2% |
| SDS | 2% |
| Magnesium percarbonate | 19% |
| Bleaching mixture B | |
| Potassium persulfate | 56% |
| Sodium persulfate | 3% |
| Silica | 2.7% |
| SDS | 1% |
| Hydrated silica | 1% |
| EDTA | 1% |
| Sodium metasilicate | 35.3% |
| Bleaching mixture C | |
| Ammonium persulfate | 5% |
| Potassium persulfate | 40% |
| Sodium persulfate | 10% |
| Guar gum | 3% |
| Hydrated silica | 7% |
| Silica | 3% |
| Glyceryl stearate | 2% |
| EDTA | 0.5% |
| SDS | 1% |
| Magnesium percarbonate | 15% |
| Sodium metasilicate | 13.5% |
| Bleaching mixture D | |
| Ammonium persulfate | 10% |
| Potassium persulfate | 40% |
| Sodium persulfate | 10% |
| Hydroxyethylcellolose | 3% |
| Hydrated silica | 7% |
| Silica | 3% |
| Glyceryl stearate | 1% |
| EDTA | 0.25% |
| SDS | 0.5% |
| Sodium percarbonate | 15% |
| Sodium metasilicate | 10.25% |
| Bleaching mixture E | |
| Ammonium persulfate | 15% |
| Potassium persulfate | 35% |
| Sodium persulfate | 10% |
| Hydroxyethylcellolose | 3% |
| Hydrated silica | 7% |
| Silica | 3% |
| Glyceryl stearate | 1% |
| EDTA | 0.25% |
| SDS | 0.5% |
| Sodium percarbonate | 10.25% |
| Sodium metasilicate | 15% |

Note:
percents are by weight of the total bleaching mixture (dry).

Example 6

Skin Removal

The skin was removed from a fish fillet. The fish skin was substantially descaled by scraping the surface of the fish skin with a steel wire brush and knife.

Freezing

The skin was frozen in a quick freezer (i.e. placed directly in a freezer at −80° C.). The skin was then taken out of the freezer and thawed at room temperature for about 2 h.

Decellularization a) The tissue was incubated in a solution of 0.5% TRITON® X-100 and 0.02% sodium azide in Dulbecco's Phosphate Buffered Saline (DPBS), shaken at 40 rpm for 2 h at room temperature, and the solution was poured off.

b) The de-scaling process was continued with a knife. The result was a scale free product (no visible scales).

c) The tissue was then put in 2 mM L-Glutamine in Hank's Balanced Salt Solution (HBSS) for 10 min at 40 rpm and room temperature, and the solution was poured off.
d) The tissue was put in a solution of 0.5% Sodium Dodecyl Sulfate (SDS) in HBSS for 1 h at room temperature, shaken at 40 rpm, and the solution was poured off.

Digestion

The tissue was incubated for 18 h at room temperature in a digestion solution of 1 mM EDTA and 0.05 µg/mL trypsin, at a pH of 8.5.

Bleaching

The tissue was bleached with bleaching mixture C and 2% hydrogen peroxide for 30 minutes.

Washing

The tissue was washed in a continuous water flow for 48 hours at 6° C.

Cryoprotection

The fish skin was immersed in a pre-freezing solution containing 7% dextran, 6% sucrose, 6% raffinose and 1 mM EDTA in Dulbecco's Phosphate Buffered Saline (DPBS).

Packaging

The fish skin was inserted into a TYVEK® membrane pouch and heat sealed shut.

Lyophilization

The pouch containing the fish skin was inserted into a freeze dryer and freeze dried.

Sterilization

The pouch containing the fish skin was inserted into an ethylene oxide chamber and treated with 1 to 5 cycles of ethylene oxide to sterilize the scaffold.

Example 7

The product was produced as in Example 6 apart from the freezing step after skin removal. Instead of the freezing step the tissue was washed two times for 1 h at 4° C. with sterile phosphate-buffered saline containing 50 mM ascorbic acid, 500 ppm streptomycin, respectively.

Example 8

Skin Removal

The skin was removed from a fish fillet. The fish skin was descaled by scraping the surface of the fish skin with a steel wire brush and knife.

Freezing

The skin was frozen in a quick freezer at −80° C.). The skin was then taken out of the freezer and thawed at room temperature for about 2 h.

Decellularization
a) The tissue was incubated in a solution of 0.5% TRITON® X-100 and 0.02% EDTA in Dulbecco's Phosphate Buffered Saline (DPBS), shaken at 40 rpm for 24 h at room temperature, and the solution was poured off
b) The de-scaling process was continued with a knife The result was a scale free-product (no visible scales).
c) The tissue was put in a solution of 0.5% Sodium Dodecyl Sulfate (SDS) in HBSS for 1 h at room temperature, shaken at 40 rpm, and the solution was poured off.
d) The tissue was then put in 2 mM L-Glutamine in Hank's Balanced Salt Solution (HBSS) for 10 min at 40 rpm and room temperature, and the solution was poured off.

Bleaching

The tissue was bleached with bleaching mixture C and 2% hydrogen peroxide for 30 minutes.

Washing

The tissue was washed in a continuous water flow for 48 hours at 6° C.

Cryoprotection

The fish skin was immersed in a pre-freezing solution containing 7% dextran, 6% sucrose, 6% raffinose and 1 mM EDTA in Dulbecco's Phosphate Buffered Saline (DPBS).

Packaging

The fish skin was inserted into a TYVEK® membrane pouch and heat sealed shut.

Lyophilization

The pouch containing the fish skin was inserted into a freeze dryer and freeze dried.

Sterilization

The pouch containing the fish skin was inserted into an ethylene oxide chamber and treated with 1 to 5 cycles of ethylene oxide to sterilize the scaffold.

Example 9

The product was produced as in Example 8 apart from the freezing step after skin removal. Instead of the freezing step the tissue was washed two times for 1 h at 4° C. with sterile phosphate-buffered saline containing 50 mM ascorbic acid, 500 ppm streptomycin, respectively.

Example 10

Skin Removal

The skin was removed from a fish fillet. The fish skin was descaled by scraping the surface of the fish skin with a steel wire brush and knife.

Freezing

The skin was frozen in a quick freezer at −80° C. The skin was then taken out of the freezer and thawed at room temperature for about 2 h.

Decellularization
a) The tissue was incubated in a solution of 0.5% TRITON® X-100 and 0.02% EDTA in Dulbecco's Phosphate Buffered Saline (DPBS), shaken at 40 rpm for 48 h at room temperature, and the solution was poured off
b) The tissue was then put in 2 mM L-Glutamine in Hank's Balanced Salt Solution (HBSS) for 10 min at 40 rpm and room temperature, and the solution was poured off.

Bleaching

The tissue was bleached with Kerecis bleaching mixture C and 2% hydrogen peroxide for 30 minutes.

Washing

The tissue was washed in a continuous water flow for 12 hours at 6° C.

Cryoprotection

The fish skin was immersed in a pre-freezing solution containing 7% dextran, 6% sucrose, 6% raffinose and 1 mM EDTA in Dulbecco's Phosphate Buffered Saline (DPBS).

Packaging

The fish skin was inserted into a TYVEK® membrane pouch and heat sealed shut.

Lyophilization

The pouch containing the fish skin was inserted into a freeze dryer and freeze dried.

Sterilization

The pouch containing the fish skin was inserted into an ethylene oxide chamber and treated with 1 to 5 cycles of ethylene oxide to sterilize the scaffold.

Example 11

The product was produced as in Example 10 apart from the freezing step after skin removal. Instead of the freezing step the tissue was washed two times for 1 h at 4° C. with sterile phosphate-buffered saline containing 50 mM ascorbic acid, 500 ppm streptomycin, respectively.

Example 12

Skin Removal

The skin was removed from a fish fillet. The fish skin was descaled by scraping the surface of the fish skin with a steel wire brush and knife. The result was a scale free product.
Freezing The skin was frozen in a quick freezer at −80° C. The skin was then taken out of the freezer and thawed at room temperature for about 2 h.
Decellularization and Bleaching
a) The tissue was incubated with bleaching mixture C and 2% hydrogen peroxide for 30 minutes.
b) The tissue was put in a solution of 0.5% Sodium Dodecyl Sulfate (SDS) in HBSS for 1 h at room temperature, shaken at 40 rpm, and the solution was poured off.
c) The tissue was then put in 2 mM L-Glutamine in Hank's Balanced Salt Solution (HBSS) for 10 min at 40 rpm and room temperature, and the solution was poured off.
Washing The tissue was washed in a continuous water flow for 12 hours at 6° C.
Cryoprotection The fish skin was immersed in a pre-freezing solution containing 7% dextran, 6% sucrose, 6% raffinose and 1 mM EDTA in Dulbecco's Phosphate Buffered Saline (DPBS).
Packaging The fish skin was inserted into a TYVEK® membrane pouch and heat sealed shut.
Lyophilization The pouch containing the fish skin was inserted into a freeze dryer and freeze dried.
Sterilization The pouch containing the fish skin was inserted into an ethylene oxide chamber and treated with 1 to 5 cycles of ethylene oxide to sterilize the scaffold.

Example 13

The product was produced as in Example 12 apart from the freezing step after skin removal. Instead of the freezing step the tissue was washed two times for 1 h at 4° C. with sterile phosphate-buffered saline containing 50 mM ascorbic acid, 500 ppm streptomycin, respectively.

Example 14

The thickness of the product was measured before and after lyophilization. Thickness was measured with a digital caliper. The average thickness before and after lyophilization was 0.29 mm and 0.46 mm, respectively. The product can be rehydrated (e.g. in a salt water solution) after lyophilization and before use on a wound. When lyophilized and rehydrated product was tested, the average thickness was 0.30 mm. The water loss (based on weight differential before and after lyophilization) was calculated to be about 80-82%.

Example 15

The permeability of the product was measured under atmospheric pressure and under vacuum (0.2 atm.) Average permeability under atmospheric pressure was 3.73 mg of water per square mm sample per 24 hrs. Average permeability under vacuum was 4.93 mg of water per square mm sample per 180 sec.

Example 16

Preliminary biodegradability tests were performed by incubating samples of the product in either isotonic salt water or in Dulbecco's Modified Eagle Medium (DMEM) (Gibco) at 32° C. After about 6-10 days the samples degraded by more than 50% (by weight).

Example 17

Preliminary cytotoxicity tests were performed by incubating samples of the product with human foreskin fibroblast cells (cell line Hs27, ATCC CRL-1634) in DMEM, glucose, and 10% fetal bovine serum. The samples did not cause any observable phenotypic changes, diminishment, or cell death.

Example 18

The product was tested to determine yield strength, tensile strength, and elongation. Uniform samples measuring 33 mm by 6 mm were rehydrated and secured in grips at 0.4 bar pressure in a 500 N load cell. Samples were kept wet for the duration of the testing. Results are shown in Table 1 below:

TABLE 1

| Sample # | Sample thickness [mm] | Max. force [N] | Elongation at max. stress [mm] | Max. strain [%] | Stress at max. force [Mpa] |
|---|---|---|---|---|---|
| 1 | 0.48 | 18.10 | 11.68 | 35.4% | 6.5 |
| 2 | 0.63 | 34.52 | 10.67 | 32.3% | 9.2 |
| 3 | 0.35 | 26.66 | 13.53 | 41.0% | 12.0 |
| 4 | 0.45 | 8.70 | 11.32 | 34.3% | 3.1 |
| 5 | 0.56 | 75.59 | 20.52 | 62.2% | 22.7 |
| 6 | 0.76 | 86.00 | 21.85 | 66.2% | 19.0 |
| 7 | 0.76 | 64.80 | 27.32 | 82.8% | 14.3 |
| 8 | 0.77 | 69.75 | 18.71 | 57.0% | 15.0 |
| 9 | 0.33 | 23.67 | 11.66 | 35.3% | 11.74 |
| 10 | 0.29 | 6.91 | 17.02 | 51.6% | 4.51 |

Note:
1 Mpa (Mega Pascal) = 1 N/mm$^2$

The scaffold material described herein is stronger and stretches considerably more than acellular matrix grafts made from urinary bladders from rats, pigs, and humans (see Dahms et al., *Composition and biomechanical properties of the bladder acellular matrix graft: comparative analysis in rat, pig and human*. British Journal of Urology. 1998; 82(3): 411-419) and the FDA-approved ALLODERMDERM® (see Bottino et al., *Freeze-dried acellular dermal matrix graft: Effects of rehydration on physical, chemical, and mechanical properties*. Dental Materials. 2009; 25(9):1109-1115).

Attempts were made at testing the tensile strength of OASIS® (porcine small intestine submucosa) and MATRISTEM™ (porcine urinary bladder), but samples of both products disintegrated before any measurements could be made.

What is claimed is:

1. A scaffold material, comprising intact decellularized fish skin, wherein the intact decellularized fish skin comprises extracellular matrix material and up to about 25% (weight/weight) lipids from the intact decellularized fish skin.

2. The scaffold material of claim 1, wherein the scaffold material is in the form of at least one of a wound dressing, bandage, suture material, or mesh material.

3. The scaffold material of claim 1, wherein the scaffold material is substantially scale-free.

4. The scaffold material of claim 1, wherein the scaffold material is biocompatible.

5. The scaffold material of claim 1, wherein the scaffold material further comprises one or more added active agents.

6. The scaffold material of claim 4, wherein the added active agent is selected from the group consisting of antibiotics, antiseptics, antimicrobial agents, antivirals, antifungals, antiparasitics, anti-inflammatory agents, antioxidants, drugs, proteins, peptides, and combinations thereof.

7. A method for producing a scaffold material, comprising: (a) obtaining a fish skin; and (b) decellularizing the fish skin to obtain intact decellularized fish skin that includes substantially intact extracellular matrix material and up to about 25% (weight/weight) lipids from the intact decellularized fish skin.

8. The method of claim 7, further comprising de-scaling, washing, freezing, bleaching, digesting, and/or cryopreserving the fish skin.

9. The method of claim 7, wherein decellularizing comprises one or more physical treatment, one or more chemical treatment, one or more enzymatic treatment, or any combination thereof.

10. The method of claim 9, wherein the chemical treatment comprises treating the fish skin with one or more decellularizing agents selected from the group consisting of ionic salts, bases, acids, detergents, oxidizing agents, hypertonic solutions, chelating agents, organic solvents, methionine, cysteine, maleic acid, polymers that bind to DNA, and combinations thereof.

11. The method of claim 9, wherein the enzymatic treatment comprises treating the fish skin with one or more enzyme selected from the group consisting of proteases, endonucleases, and exonucleases.

12. The scaffold material of claim 1, wherein the lipids include omega-3 fatty acids.

13. The scaffold material of claim 12, wherein the omega-3 fatty acids include at least one of eicosapentaenoic acid (EPA) or docosahexaenoic acid (DHA).

* * * * *